United States Patent
Na et al.

(10) Patent No.: US 11,628,164 B2
(45) Date of Patent: Apr. 18, 2023

(54) COMPOSITION CONTAINING SALSOLINOL FOR TREATING LIVER CANCER

(71) Applicant: SUNGSHIN WOMEN'S UNIVERSITY R&DB FOUNDATION, Seoul (KR)

(72) Inventors: Hye Kyung Na, Seoul (KR); Hong Kyung Yang, Seoul (KR); Hyun Jung Choi, Ulsan (KR)

(73) Assignee: Sungshin Women's University R&DB Foundation, Seoul (KR)

( * ) Notice: Subject to any disclaimer, the term of this patent is extended or adjusted under 35 U.S.C. 154(b) by 294 days.

(21) Appl. No.: 17/091,124

(22) Filed: Nov. 6, 2020

(65) Prior Publication Data
US 2022/0110930 A1 Apr. 14, 2022

(30) Foreign Application Priority Data
Oct. 13, 2020 (KR) .................. 10-2020-0131855

(51) Int. Cl.
*A61K 31/47* (2006.01)
*A61P 35/00* (2006.01)

(52) U.S. Cl.
CPC ............ *A61K 31/47* (2013.01); *A61P 35/00* (2018.01)

(58) Field of Classification Search
CPC ........ A61K 31/47; A23L 29/045; A61P 35/00
See application file for complete search history.

(56) References Cited

U.S. PATENT DOCUMENTS

2014/0080775 A1* 3/2014 Moon ............... A61P 31/18 514/357
2015/0335634 A1* 11/2015 Lee ................ A61K 31/472 514/307

FOREIGN PATENT DOCUMENTS

KR 10-2019-0129765 A 11/2019

OTHER PUBLICATIONS

Kurnik-Lucka; Neurotox Res. 2018, 33, 485-514. DOI 10.1007/s12640-017-9818-6 (Year: 2018).*
Melzig; Journal of Ethnopharmacology 2000, 73, 153-159. https://doi.org/10.1016/S0378-8741(00)00291-9 (Year: 2000).*
KR20190129765; EPO Machine Translation. Published in Korean Language on Nov. 20, 2019. (Year: 2019).*
Kurnik-Lucka; Neurotox Res. 2020, 37, 286-297. https://doi.org/10.1007/s12640-019-00118-7 (Year: 2020).*
Wang; Cancers 2019, 11(7), 926; https://doi.org/10.3390/cancers11070926 (Year: 2019).*
Connor, J. (2017) "Alcohol intake as a cause of cancer.", *Addiction*, 112(2):222-228. doi:10.1111/add.13477.
DeCuypere, M., et al. (2008) "Regional distribution of tetrahydroisoquinoline derivatives in rodent, human, and Parkinson's disease brain.", *J Neurochem.*, 107(5):1398-1413. doi:10.1111/j.1471-4159.2008.05709.x.
Haber, H., et al. (1996) "Plasma and urine the salsolinol in humans: effect of acute ethanol intake on enantiomeric composition of salsolinol.", *Alcohol Clin Exp Res.*, 20(1):87-92. doi:10.1111/j.1530-0277.1996.tb01049.x.
Murata, M., et al. (2013) "Oxidative DNA damage and mammary cell proliferation by alcohol-derived the salsolinol.", *Chem Res Toxicol.*, 26(10):1455-1463. doi:10.1021/tx400182n.
Quintanilla, ME., et al. (2007) "Sex differences, alcohol dehydrogenase, acetaldehyde burst, and aversion to ethanol in the rat: a systems perspective.", *Am J Physiol Endocrinol Metab.*, 293(2):E531-E537. doi:10.1152/ajpendo.00187.
Rommelspacher, H., et al. (1995) "Determination of (R)- and (S)-salsolinol sulfate and dopamine sulfate levels in plasma of nonalcoholics and alcoholics.", *Alcohol.*, 12(4):309-315. doi:10.1016/0741-8329(95)00004-b.

* cited by examiner

*Primary Examiner* — Daniel R Carcanague

(74) *Attorney, Agent, or Firm* — Harness, Dickey & Pierce, P.L.C.

(57) ABSTRACT

Salsolinol is a metabolite of alcohol and is cytotoxic, so that the salsolinol has been studied as a diagnostic biomarker for a liver disease and a liver cancer, but the salsolinol has not been reported as a therapeutic agent for the liver disease or the liver cancer. Since the salsolinol regulates tumor-related genes and inflammation-related genes specifically for men, it is experimentally found that the salsolinol has an effect of alleviating a liver cancer and an alcoholic hepatitis. Therefore, the salsolinol is contained together with a pharmaceutically acceptable salt as an effective ingredient and is provided as a pharmaceutical composition for treating the liver cancer or a health functional food for preventing and improving the alcoholic liver disease to have an effect of treating the liver disease and the liver cancer or preventing and improving the liver disease and the liver cancer.

7 Claims, 14 Drawing Sheets

COMPOSITION CONTAINING SALSOLINOL FOR TREATING LIVER CANCER

CROSS-REFERENCE TO RELATED PATENT APPLICATION

This application claims the benefit of Korean Patent Application No. 10-2020-0131855, filed on Oct. 13, 2020, in the Korean Intellectual Property Office, the disclosure of which is incorporated herein by reference in its entirety by reference.

FIELD

The invention relates to a composition for treating a liver cancer containing salsolinol as an effective ingredient and inhibits expression of oncogenes and proteins, and increases expression of anti-inflammatory genes to treat or prevent and improve an alcoholic liver disease and a liver cancer.

BACKGROUND

Alcohol intake is known to be a major cause of human cancers such as a breast cancer, a stomach cancer, a colon cancer, and a liver cancer, and an alcohol-induced cancer accounts for 5.8% of all cancer deaths worldwide (Connor J. 2017). A small amount of ingested alcohol is decomposed in the stomach, and alcohol absorbed from the small intestine through the stomach is moved to the liver through the blood vessels. 90% or more of the alcohol moved to the liver is decomposed, but 2% to 5% of the alcohol that is not decomposed is excreted through the urine.

The alcohol carried to the liver is decomposed into acetaldehyde through two pathways of alcohol dehydrogenase or microsomal ethanol oxidizing system (MEOS), and the acetaldehyde is metabolized to a non-toxic acetic acid by (acetaldehyde dehydrogenase). The acetic acid is converted to acetyl-CoA through another metabolic process to be used for energy synthesis, or to be used for cholesterol and fatty acid synthesis and ketone formation.

The reactivity to the alcohol differs by sex, and the reactivity is determined the alcohol dehydrogenase. The expression level and activity of the alcohol dehydrogenase differ by males and females. The activity of the alcohol dehydrogenase in female liver tissue is 70% higher than that in male liver tissue, and as a result, the level of acetaldehyde in blood is higher in female (Quintanilla M E, et al., 2007).

The salsolinol (6,7-dihydroxy-1-methyl-1,2,3,4-tetrahydroisoquinoline) is a dopamine-derived catechol isoquinoline. The salsolinol is produced by polymerization of acetaldehyde with dopamine by the salsolinol synthase. When the amount of the salsolinol increases in the cell, release of active oxygen species (ROS) in the mitochondria is increased, which induces cell damage. And thus, the increase of the salsolinol is recognized as a pathological factor in Parkinson's disease and alcoholic poisoning (DeCuypere M, et al., 2008; Rommelspacher H, et al., 1995).

An alcohol dehydrogenase, which decomposes alcohol, is mainly present in the mitochondria. Therefore, acetaldehyde produced during the decomposition of alcohol by alcohol dehydrogenase is mainly located in the mitochondria. The acetaldehyde formed in the mitochondria directly binds to mitochondrial proteins, nucleic acids, phospholipids, or dopamine, and ROS generated in the alcohol decomposing process oxidizes lipids, so that 4-hydroxynonenal and malondialdehyde are produced. At this time, 4-hydroxynonenal and malondialdehyde have an effect of inhibiting the activity of acetaldehyde dehydrogenase, and thus, acetaldehyde which is harmful to cells cannot be converted into a harmless acetic acid, so that cytotoxicity is exhibited. The concentration of the salsolinol, produced by polymerization of acetaldehyde and dopamine, is increased in the blood and urine of a normal person who took ethanol acutely (Haber H, et al., 1996).

A liver cancer is outbroken by hepatitis B, hepatitis C, chronic liver disease, and alcohol intake, and the like, and alcoholic hepatitis and cirrhosis are strong inducing factors of the liver cancer. As alcohol-induced cancer incidence, there are known various causes such as polymorphism of alcohol dehydrogenase related ton alcohol metabolism, decomposition with folic acid, generation of active oxygen species due to increased expression of Cytochrome P450 2E1 (CYP2E1) by alcohol intake, DNA damage and DNA adduct generation due to active oxygens, increased expression of cytokines related to inflammatory response, increased absorption of carcinogens due to tissue damage, and increased angiogenesis.

KR10-2019-0129765 discloses a method for diagnosing the liver disease or the liver cancer by measuring the concentration of salsolinol and comparing the result with the concentration of salsolinol in a normal entity. KR10-2019-0129765 experimentally discloses that the salsolinol increases fibrosis-related genes and active oxygen species in normal hepatocytes (NCTC1469), and PARP-cleavage is induced to induce apoptosis. However, KR10-2019-0129765 discloses that the salsolinol exhibits cytotoxicity against male-derived liver cancer cell lines (SK-Hep1), but at the same time, it is confirmed that the salsolinol increases signal transducer and transcription 3 (STAT3) phosphorylation, which induces the proliferation of cancer cells and it is confirmed that the expression of HO-1, an antioxidant-related gene, is increased, so that there is a limitation that the result of whether or not the salsolinol kills liver cancer cells is not clear.

As a result of studies of salsolinol related to cancer, there is a study that illustrates that the salsolinol induces proliferation of breast cancer cells (Murata M, et al., 2013), but this is merely a result of a basic study, and there has not been reported studies related to liver cancer.

Patent documents and reference Documents mentioned in this specification are incorporated herein by reference to the same extent as if each document is individually and explicitly specified by reference.

Patent Document: KR 10-2019-0129765

Non-patent Document:

Connor J. Alcohol intake as a cause of cancer. Addiction. 2017; 112(2):222-228. doi:10.1111/add.13477.

Quintanilla M E, Tampier L, Sapag A, Gerdtzen Z, Israel Y. Sex differences, alcohol dehydrogenase, acetaldehyde burst, and aversion to ethanol in the rat: a systems perspective. Am J Physiol Endocrinol Metab. 2007; 293 (2):E531-E537. doi:10.1152/ajpendo.00187.2007.

DeCuypere M, Lu Y, Miller D D, LeDoux M S. Regional distribution of tetrahydroisoquinoline derivatives in rodent, human, and Parkinson's disease brain. J Neurochem. 2008; 107(5):1398-1413. doi:10.1111/j.1471-4159.2008.05709.x.

Rommelspacher H, Sllstrom Baum S, Dufeu P, Schmidt L G. Determination of (R)- and (S)-salsolinol sulfate and dopamine sulfate levels in plasma of nonalcoholics and alcoholics. Alcohol. 1995; 12(4):309-315. doi:10.1016/0741-8329(95)00004-b.

Haber H, Winkler A, Putscher I, et al. Plasma and urine the salsolinol in humans: effect of acute ethanol intake on enantiomeric composition of salsolinol. Alcohol Clin Exp Res. 1996; 20(1):87-92. doi:10.1111/j.1530-0277.1996.tb01049.x.

Murata M, Midorikawa K, Kawanishi S. Oxidative DNA damage and mammary cell proliferation by alcohol-derived the salsolinol. Chem Res Toxicol. 2013; 26(10): 1455-1463. doi:10.1021/tx400182n.

SUMMARY

In the invention, it is experimentally confirmed that salsolinol inhibits phosphorylation of STAT3, phosphorylation of AKT, expression of Annexin 2, expression of proliferating cell nuclear antigen (PCNA), expression of Ki-67, expression of 8-OHdG, expression of E-cadherin, and expression of Vimentin and increases expression of 15-PGDH and expression of p53 in liver cancer cell lines and liver cancer animal models to inhibit proliferation, so that the alcoholic liver disease can be alleviated and the liver cancer can be treated.

Accordingly, an object of the invention is to provide a pharmaceutical composition for treating a liver cancer and a health functional food for preventing and improving an alcoholic liver disease containing the salsolinol as an effective ingredient.

Other objects and technical features of the invention are presented in more detail with reference to the following detailed description, the claims, and the drawings.

According to an aspect of the invention, there is provided a pharmaceutical composition for treating a liver cancer, containing salsolinol as an effective ingredient and a health functional food for preventing and improving an alcoholic liver disease.

The pharmaceutical composition for treating the liver cancer and the health functional food for preventing and improving the alcoholic liver disease has a specific therapeutic effect on a male-derived liver cancer and liver disease and inhibiting phosphorylation of STAT3, phosphorylation of AKT, expression of Annexin 2, expression of PCNA, expression of Ki-67, expression of 8-OHdG, expression of E-cadherin, and expression of Vimentin and increasing expression of HO-1, expression of 15-PGDH, and expression of p53.

The salsolinol according to the invention has cytotoxicity as a metabolite of alcohol, so it has been studied as a diagnostic biomarker for a liver disease and a liver cancer, but has not been reported as a therapeutic agent for the liver disease or the liver cancer. According to the invention, it is experimentally found that since the salsolinol regulates tumor-related genes and inflammation-related genes specifically for men, the salsolinol has the effect of alleviating the liver cancer and the alcoholic hepatitis.

Therefore, the salsolinol according to the invention is contained together with a pharmaceutically acceptable salt as an effective ingredient and is provided as a pharmaceutical composition for treating the liver cancer or a health functional food for preventing and improving the alcoholic liver disease to have an effect of treating the liver disease and the liver cancer or preventing and improving the liver disease and the liver cancer.

DETAILED DESCRIPTION

Figure 1A:
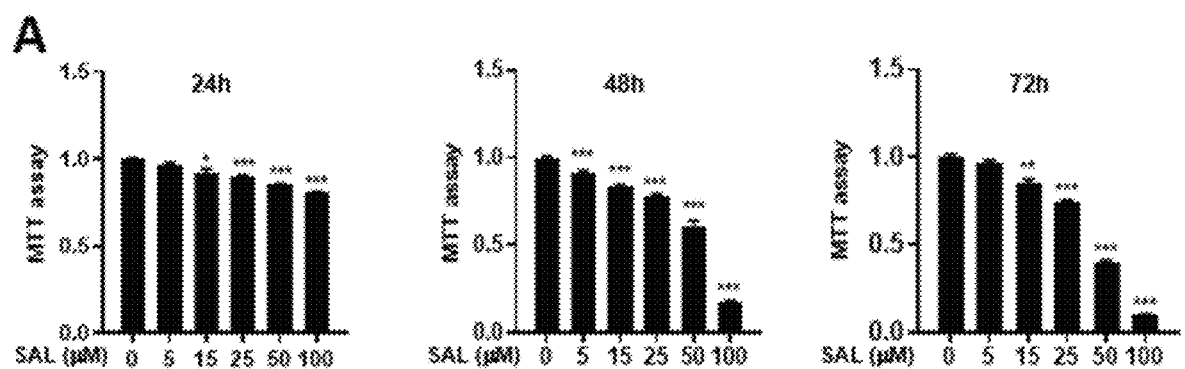
FIGS. 1A and 1B illustrate results of confirming a change in cell viability of male-derived liver cancer cell lines (SK-Hep1) and female-derived liver cancer cell lines (SNU387) according to a concentration of salsolinol according to the invention.

The invention provides a pharmaceutical composition containing salsolinol (SAL, 6,7-dihydroxy-1-methyl-1,2,3,4-tetrahydroisoquinoline) as an effective ingredient for treating a liver cancer or a health functional food for preventing and improvement an alcoholic liver disease.

The salsolinol has cytotoxicity as a metabolite of alcohol and denotes a metabolite formed by polymerization of acetaldehyde, which is a major metabolite of alcohol, with dopamine present in peripheral tissues by a salsolinol synthase. The salsolinol is recognized as a pathological factor related to Parkinson's disease and alcoholic poisoning because when the amount of salsolinol increases in cells, the salsolinol increases mitochondrial release of active oxygen species (ROS) and induces cell damage. The salsolinol has been mainly studied on damage to brain tissues due to alcohol intake, and recently, it has been reported that the salsolinol increases the concentration of active oxygen in cells to induce cell proliferation of breast cancer. Any research has not been reported as a therapeutic agent related to liver disease and liver cancer yet.

KR10-2019-0129765 discloses that, by measuring the concentration of salsolinol from the biological sample and comparing the result with that in a normal entity, the liver disease or the liver cancer can be diagnosed. KR10-2019-0129765, through Examples, illustrates that when the normal hepatocytes are treated with the salsolinol salsolinol, the increase in the expression level of factors related to inflammation and the presence of the cytotoxicity indicate that, when the concentration of salsolinol is high, there is a possibility that the liver damage or the liver cancer may occur. According to the example of KR10-2019-0129765, it is confirmed that when the liver cancer cell lines are treated with the salsolinol, the proliferation of liver cancer cell lines is inhibited. However, in another embodiment of KR10-2019-0129765, the expression of antioxidant-related factors (HO-1 and 15-PGDH) in liver cancer cell lines is increased by the salsolinol, and phosphorylation of STAT3 which is an oncogene is increased, and the activity of STAT3 is confirmed to be increased. This can be interpreted as protecting liver cancer cell lines from external stimuli such as active oxygen species by the increased antioxidant-related factors by the salsolinol, and since the activity of the STAT3 is increased, this can be interpreted as further increasing the activity of cells. Therefore, it is determined that it cannot be concluded from only the results of KR10-2019-0129765 that the salsolinol can reduce the activity of liver cancer cell lines and treat the liver cancer.

In the invention, it is demonstrated by using liver cancer cell lines and a liver cancer induction mouse model that the salsolinol has a therapeutic effect on the liver cancer.

According to an embodiment of the invention, the pharmaceutical composition for treating the liver cancer containing the salsolinol according to the invention as an effective ingredient is characterized to inhibit phosphorylation of STAT3, phosphorylation of AKT, expression of Annexin 2, expression of PCNA, expression of Ki-67, expression of 8-OHdG, expression of SNAI2, and expression of Vimentin and to increase expression of 15-PGDH and expression of p53, so that the pharmaceutical composition inhibits proliferation of male-derived liver cancer cells. In particular, according to the embodiment of the invention, after treatment of the male-derived liver cancer cell lines with the salsolinol, it is confirmed that the phosphorylation of STAT3 is rapidly increased initially, but it is rapidly decreased after 24 hours. In KR10-2019-0129765, after treating the liver cancer cell lines with the salsolinol, phosphorylation of STAT3 is confirmed at 24 hours. Therefore, it is determined that the results of Examples of KR10-2019-0129765 are consistent with the results of increasing phosphorylation of STAT3 at the beginning of treatment with the salsolinol according to the invention. Therefore, the invention is the results of confirming the effect of inhibiting the proliferation of the liver cancer cell lines by the salsolinol, which cannot be confirmed from KR10-2019-0129765. This effect is supported through a liver cancer induction mouse model experiment which is another embodiment of the invention.

The liver cancer refers to a malignant tumor arising from hepatocytes constituting the liver, and specifically, the liver cancer refers to a cancerous alcoholic liver disease.

The alcoholic liver disease is a disease caused by damage to hepatocytes by alcohol and includes a liver cancer arising due to worsening of an alcoholic fatty liver, alcoholic hepatitis, cirrhosis, and a liver disease.

The pharmaceutical composition for treating the liver cancer refers to a pharmaceutical composition for treating the liver cancer, and the treatment for the liver cancer refers to any action in which symptoms of the liver cancer get better or are advantageously changed.

The pharmaceutical composition may further include an appropriate carrier, excipient, and diluent commonly used in manufacturing of the pharmaceutical compositions. As the carrier, the excipient, and the diluent, there are lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils. On the other hand, the pharmaceutical composition according to the invention formulated in a form of oral dosage forms such as powders, granules, tablets, capsules, suspensions, emulsions, syrups, and aerosols, external preparations, suppositories, and sterile injectable solutions, respectively, according to methods in the related art can be used. In the case of formulation, the pharmaceutical composition is manufactured by using diluents or excipients such as generally used fillers, extenders, binders, wetting agents, disintegrants, and surfactants. Solid preparations for oral administration include tablets, pills, powders, granules, capsules, and the like. Such solid preparations are manufactured by mixing at least one excipient such as starch, calcium carbonate, sucrose, and lactose with an extract of the mixture. In addition, in addition to simple excipients, lubricants such as magnesium stearate and talc are also used. Liquid preparations for oral use include suspensions, liquid solutions, emulsions, syrups, or the like. In addition to water and liquid paraffin which are commonly used simple diluents, various excipients such as wetting agents, sweetening agents, flavoring agents, and preservatives may be included. Formulations for parenteral administration include sterile aqueous solutions, non-aqueous solvents, suspensions, emulsions, lyophilized formulations, and suppositories. As the non-aqueous solvents and suspensions, propylene glycol, polyethylene glycol, vegetable oil such as olive oil, and injectable ester such as ethyl oleate may be used. As a base for suppositories, witepsol, macrogol, tween 61, cacao butter, laurin butter, glycerogelatin, and the like may be used.

The health functional food for preventing and improving the alcoholic liver disease has an effect of delaying the outbreak of the alcoholic liver disease or improving the symptoms of the alcoholic liver disease.

The health functional food refers to a food manufactured and processed in the form of tablets, capsules, powders, granules, liquids, pills or the like by using raw materials or ingredients having useful functions for the human body. The health functional foods include drinks, meat, sausage, bread, biscuits, rice cakes, chocolate, candy, snacks, confectionery, pizza, ramen, other noodles, gum, dairy products including ice cream, various soups, beverages, alcoholic beverages, vitamin complex products, processed dairy products, and the like and can include all kinds of health functional foods in the usual sense. The health functional food may contain various flavoring agents or natural carbohydrates as additional ingredients. The natural carbohydrates are monosaccharides such as glucose and fructose, disaccharides such as maltose and sucrose, and polysaccharides such as dextrin and cyclodextrin, and sugar alcohols such as xylitol, sorbitol, and erythritol. As the sweetening agent, natural sweetening agents such as taumatin and stevia extract, or synthetic sweetening agents such as saccharin and aspartame can be used. In addition, various nutrients, vitamins, electrolytes, flavoring agents, coloring agents, pectic acid and salts thereof, alginic acid and salts thereof, protective colloidal thickeners, pH adjusters, stabilizers, preservatives, glycerin, alcohols, carbonates used in carbonated beverages, and the like may be further included.

According to an embodiment of the invention, a pharmaceutical composition for treating a liver cancer or a health functional food for preventing and improving an alcoholic liver disease containing the salsolinol according to the invention as an effective ingredient is characterized to have effects of specifically treating, preventing, and improving a liver cancer and is characterized to inhibit proliferation of male-derived liver cancer cells and protects hepatocytes by inhibiting phosphorylation of STAT3, phosphorylation of AKT, expression of Annexin 2, expression of PCNA, expression of Ki-67, expression of 8-OHdG, expression of SNAI2, and expression of Vimentin and increasing expression of p53.

According to another embodiment of the invention, with a pharmaceutical composition for treating a liver cancer or a health functional food for preventing and improving an alcoholic liver disease containing the salsolinol according to the invention as an effective ingredient, it is confirmed at the initial stage of treatment that phosphorylation of STAT3 that facilitates the proliferation of liver cancer cells and expression of antioxidant genes that protect the liver cancer cells from external stimuli such as ROS are increased. But as time passed, it is confirmed that the amount of phosphorylation of STAT3 is decreased, and the expression of p53 which is a gene that inhibits a cancer is increased. In addition, since the expression of 15-PGDH is increased to alleviate an inflammatory response of the male-derived hepatocellular carcinoma cells, the pharmaceutical composition is confirmed to have an effect of treating the liver cancer and preventing and improving an alcoholic liver disease.

According to an embodiment of the invention, a pharmaceutical composition for treating a liver cancer or a health functional food for preventing and improving an alcoholic liver disease containing the salsolinol according to the invention as an effective ingredient is confirmed to have effects of specifically treating, preventing, and improving a male-derived liver cancer or a male-derived alcoholic liver disease. The gender specificity of the salsolinol has been confirmed in KR10-2019-0129765. According to KR10-2019-0129765, the gene expressions of the male and female mice treated with the salsolinol are compared, and as a result, it is confirmed that liver tissue inflammation, epithelial mesenchymal metastasis, and expression of antioxidant enzymes are increased in the male mouse, and the expressions of estrogen receptor a and androgen receptor are significantly increased only in the liver tissue of the male mouse. Therefore, it is confirmed that the gender specificity of the salsolinol is related to sex hormones. The gender specificity of the salsolinol is determined to require further studies related to the sex hormones.

In the following examples, the invention will be described in detail.

EXAMPLE

1. Experimental Method 1.1. Human-Derived Liver Cancer Cell Lines and Salsolinol SK-Hep1 and SNU387, which are human-derived hepatoma cell lines, are distributed from Korea Cell Line Bank. The SK-Hep1 is derived from a male human body, and the SNU387 is derived from a female human body. The SK-Hep1 and the SNU387 are cultured in a medium including a minimum essential medium (Dulbecco Modified Eagle Medium, DMEM) (Gibco BRL grand Island, N.Y., USA) and in a medium containing 10% FBS (HyClone Lab, Inc, Logan, Utah, USA), 100 U/ml penicillin. (penicillin) and 100 μg/ml streptomycin (Gibco, Grand Island, N.Y., USA) at 37° C. in an atmosphere of 5% $CO_2$.

The salsolinol according to the invention is purchased from Abcam (Cambridge, Mass., USA) and had a purity of 99%.

1.2. MTT Experiment on Human-Derived Liver Cancer Cell Lines

The cultured liver cancer cell lines (SK-HEP1 and SNU387) are dispensed into each well of a 48-well plate so as to have a concentration of $5 \times 10^4$ cells. After culturing for 24 hours, the sample is treated with the salsolinol for 24 hours, 48 hours, and 72 hours so as to have a concentration of 5 μM, 15 μM, 25 μM, 50 μM, or 100 μM. After that, 250 μl of 0.5 mg/ml MTT solution (Sigma, St Louis, Mo., US) is added to each well and reacted at 37° C. for 1 hour. After removing the solution, MTT-formazione is lysed and washed with 250 μl of DMSO (Dimethylsulfoxide, Duksan, Gyeonggi, Korea), and then, the absorbance at 540 nm is measured by using a SpectraMax 190 microplate plate reader (Molecular Devices, LCC. San Jose, Calif.).

1.3. Colony Formation Experiment on Human-Derived Liver Cancer Cell Lines

Among the human-derived liver cancer cell lines, the SK-Hep1, which is a male-derived liver cancer cell lines, is dispensed into 96-wells so as to have a concentration of $1 \times 10^4$ cells, and then, the SK-Hep1 is treated once every two or three days so that the salsolinol has a concentration of 25 μM or 50 μM. The salsolinol-treated the SK-Hep1 is further cultured for 3 days under the above-mentioned conditions. After that, the SK-Hep1 is fixed with 4% formaldehyde, stained with crystal violet for 2 hours, and after extraction with an acetic acid, the absorbance (570 nm) is measured.

1.4. Cell Migration Assay for Human-Derived Liver Cancer Cell Lines

A culture-insert (Ibidi; Martinsried, Germany) is attached to a 24-well plate to make a 500 μm interval, and then the cultured liver cancer cell lines (SK-Hep1) are dispensed so as to have a concentration of $1.5 \times 10^5$ cells. And the culturing is performed for 24 hours. After detaching the insert from the plate, each well is treated with the salsolinol so as to have a concentration of 25 μM. After the culturing is performed for 24 hours and for 48 hours, and the sample is photographed by a microscope to check the ability of migrating cells.

1.5. Western Blotting Analysis for Human-Derived Liver Cancer Cell Lines $5 \times 10^5$ cells of Human-derived liver cancer cell lines SK-Hep1 and SNU387 are cultured in a 60 mm culture vessel, the cells are lysed, and proteins are separated through electrophoresis. And after that, western blotting analysis is performed by using a specific antibody. After treatment of the SK-Hep1 and the SNU387 with the salsolinol at different times and concentrations, the cells are washed with PBS, and the cells are scraped off with a scraper. The cells are lysed in a lysis buffer for 1 hour, and after that, centrifuge separation is performed at 13,000 rpm for 15 minutes at 4° C., and only the supernatant is extracted. 20 μg of protein contained in the supernatant is electrophoresed on SDS-polyacrylamide gel, and after that, transferred to a PVDF membrane for 2 hours. The sample reacts with antibodies pSTAT3(#9145), STAT3(#9132), PCNA(#2586), 15-PGDH (cayman No. 160615), p53(sc-126), p53(sc-99), pAKT (#9271), AKT(#9272), Annexin A2(#8235), and GAPDH (sc-32233). The protein is detected by using an enhanced chemiluminascence (ECL) detection solution.

1.6. Manufacturing DEN-Induced Liver Cancer Mouse Model and Salsolinol Administration Experiment The mouse used in the experiment are 7-week old male and female C57BL/6 mouse. The mouse is obtained from Orient Bio (ORIENT Bio, Gyeonggi-do Province, Korea) and is adapted in an environment that the contrast is controlled at a temperature of 22±2° C. and a humidity of 55 to 60% in 12-hour increments, and a standard diet is provided for 1 week. All animal experiments are performed in accordance with the regulations of the Laboratory Animal Ethics Committee of Sungshin Women's University.

After adapting a male mouse born from the mating of the adapted mouse in the same environment for 2 weeks, a DEN-induced liver cancer mouse model is generated by a method of intraperitoneally administering a liver cancer-causing substance, diethylnitrosamine (DEN, 25 mg/kg).

The salsolinol (200 mg/kg) is administered for 6 months through intraperitoneal injection three times per week from the time when the DEN-induced liver cancer mouse model (male) became 7 weeks of age. After the mouse is sacrificed, the experiment is performed.

1.7 Measurement of α-Fetoprotein for DEN-Induced Liver Cancer Mouse Model

After the experiment is completed, the experimental animals are fasted for 4 hours, sacrificed with $CO_2$ gas, and the blood collected from the heart is heparinized. And after that, centrifuge separation is performed at 3,000 rpm for 15 minutes to separate plasma.

AFP (α-Fetoprotein) analysis is measured by enzyme-linked immunosorbent assay (ELISA). The separated plasma is diluted 20 times with a diluted solution, and after that, a 50 μl of standard curve reagent and plasma are inserted into a coated 96-well plate, and after that, the culturing is performed for 2 hours at room temperature. The culture medium is removed, and washing is performed 3 times with 100 μl of wash buffer. After adding 100 μl of prepared AFP conjugate to each well, the culturing is performed for 2 hours at room temperature. The culture medium is removed, and washing is performed 3 times with 100 μl of wash buffer. After adding 100 μl of reaction reagent to each well, the culturing is performed for 30 minutes in a dark place. After adding the same amount of reaction stop reagent to each well, tapping is lightly performed to mix thoroughly. With respect to the degree of reaction, after measuring the absorbance at 450 nm, the concentration of AFP is quantified by using a standard curve of a SpectraMax 190 microplate plate reader (Molecular Devices, LCC. San Jose, Calif.).

Figure 8A:
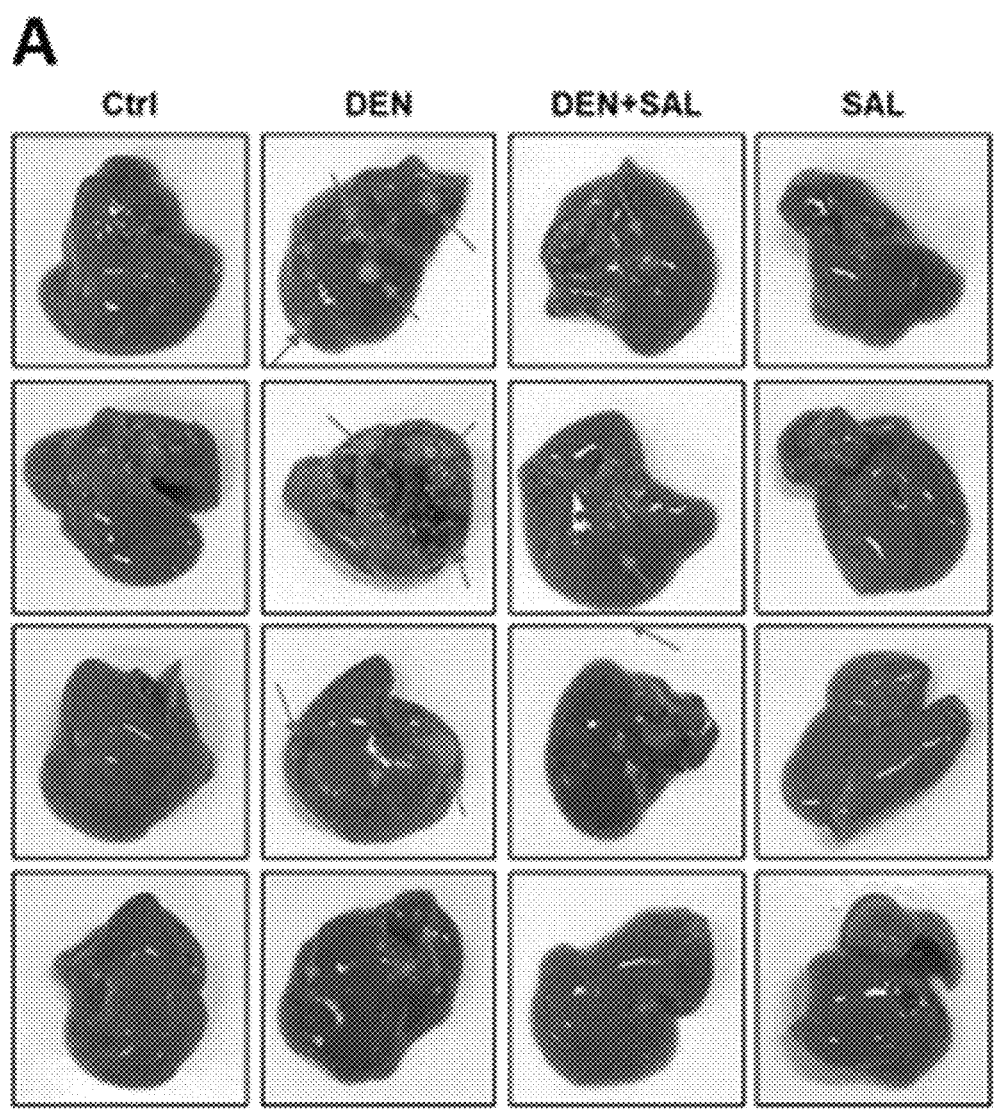
FIGS. 8A, 8B and 8C illustrate results of observation of tumor formed in a liver of a normal mouse (male) a liver of a DEN-induced liver cancer animal model (male), a liver of a DEN-induced liver cancer animal model (male) administered with salsolinol, and a liver of a normal mouse (male) administered with the salsolinol according to the invention. Panel A illustrates a cancer tissue formed on a liver surface, panel B illustrates quantitative measurement of the number of cancer tissues formed on the liver surface, and panel C illustrates results of liver tissue staining.
Figure 8B:
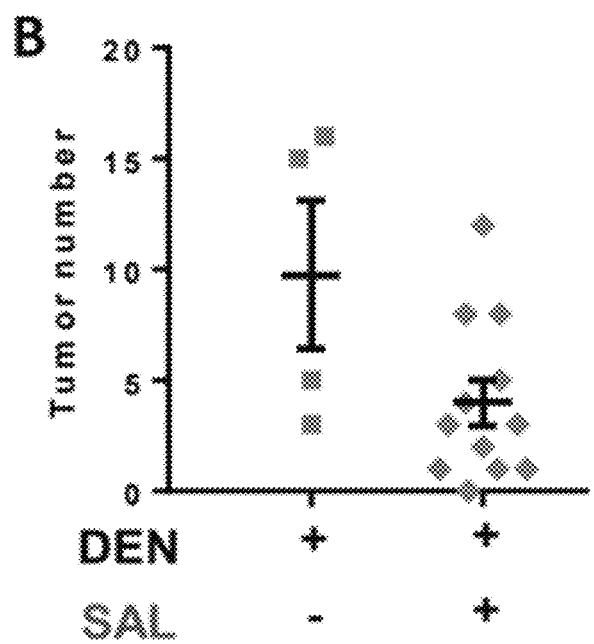
Figure 8C:
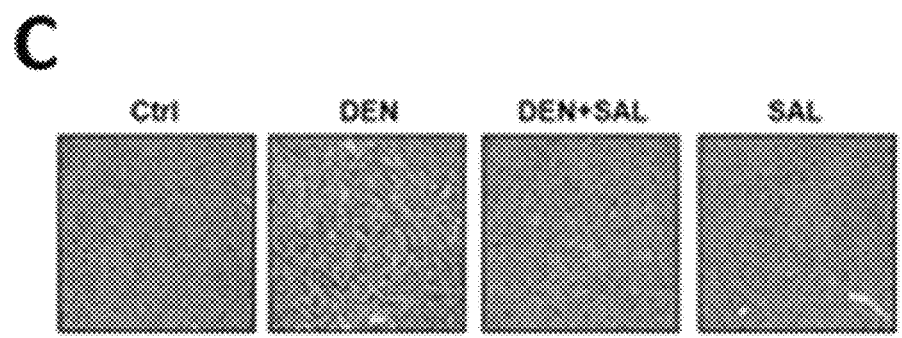

1.8. Measurement of Degree of Tumor Formation in DEN-Induced Liver Cancer Mouse Model (Experiment related to FIG. 8)

The liver tissue is separated, the number of tumors is measured, and the degree of tumor formation is illustrated by a picture. After fixing 10% formaldehyde for morphological analysis, a paraffin section slide having a thickness of 4 μm is requested to be manufactured by Notus Co., Ltd. After removing paraffin No. 3 with xylene and re-dehydration in 95% and 70% alcohol, staining is performed by using Mayer's Hematoxylin.

1.9. Immunofluorescence Staining Measurement for DEN-Induced Liver Cancer Mouse Model In the paraffin section slide requested to be manufactured by NORTHUS Co., Ltd., paraffin is removed by using xylene (Duksan, Gyeonggi, Korea). And, after a hydration process with low concentration ethanol (100, 90, 80, and 70% ethanol) at a high concentration, the slide is rinsed twice with running water. Since formaldehyde forms a cross-link between proteins to prevent a primary antibody from binding to the epitope of the antigen, the cross-link is removed by using an antigen retrieval reagent (sigma). After washing the slide thoroughly with running water, and dropping 2% triton for nuclear staining, the slide is left for 45 minutes. After washing the slide thoroughly with running water, blocking proceeds for 1 hour with a PBS solution containing 3% BSA to prevent non-specific binding. Then, after dropping a diluted PBS solution containing 3% BSA diluted with a primary antibody (8-OHdG, Ki-67) (1:500) on the slide, the slide is left at 4° C. for one day. After washing the slide with PBS and dropping a diluted secondary antibody (1:2000) on the slide, the slide is left at 4° C. for 1 hour. After washing the slide with PBS, staining with DAPI (1:200), and dropping 2-3 drops of mounting solution (sigma), the slide is covered with a slide cover. After about a day, the degree of fluorescence staining is checked by using a confocal microscope.

1.10. Real-Time Quantitative Polymerase Chain Reaction (Quantitative-PCR) of Liver Tissue in DEN-Induced Liver Cancer Mouse Model A normal mouse (M-Ctrl, n=5), a DEN-induced liver cancer mouse model (M-DEN, n=4), and a DEN-induced liver cancer mouse model treated with the salsolinol (M-DEN+SAL, n=5) are sacrificed, and liver tissues are obtained. And after that, trizol is added to lyse the liver tissues. 1 ml of a TRI reagent solution is added to the liver tissue, and after homogenization, centrifuge separation is performed at 4° C. and 12,000 rpm for 10 minutes. About 0.75 ml of the middle layer excluding the upper and lower debris is separated and put into a new tube. After adding and mixing with 0.2 ml of chloroform thoroughly, centrifuge separation is performed at 4° C. at 12,000 rcf for 15 minutes to separate 0.25 ml of the supernatant. After adding 0.25 ml of the same amount of isopropanol and leaving the sample at room temperature for 10 minutes, by performing centrifuge separation at 4° C. at 12,000 rcf for 10 minutes, RNA is precipitated.

After removing the supernatant, the RNA is washed with 75% ethanol, centrifuge separation is performed at 4° C. at 7,500 rpm for 5 minutes, and the remaining ethanol is evaporated at room temperature. The separated total RNA is quantified by using Nandrop 2000 (Thermo), and after that, cDNA is synthesized by using a reverse transcription reaction oligo dT primer and RT enzyme. By using the synthesized cDNA as a template, after addition of each primer and Bio-Rad SYBR mix (#1725270) and amplification by using a Bio-Rad Real-Time PCR instrument, analysis is performed by using quantitative software. The products amplified by real time PCR are quantified by using a comparative cycle threshold (Ct) method. Experiments are performed on an Snai1 gene (coding for SNAI1), a Vimentin gene (or VIM, coding for Vimentin), an Anxa2 gene (coding for Annexin A2), and a Col1a1 gene (coding for collagen type I alpha 1), and each sample corrected with the expression level of β-actin.

1.11. Statistic Process for Experimental Results

Experimental analysis results are represented in terms of mean±S.E. An independent sample t-test is performed for the significance between experimental groups, and comparison between experimental groups is performed by using one-way ANOVA (analysis of variance) of IBM SPSS Statistics 25. After statistic process, the significance is tested at the levels of *P<0.05, P<0.01 and *P<0.001 and plotted by using Prism 7 (Graph-pad, San Diego, Calif., USA).

Figure 1B:
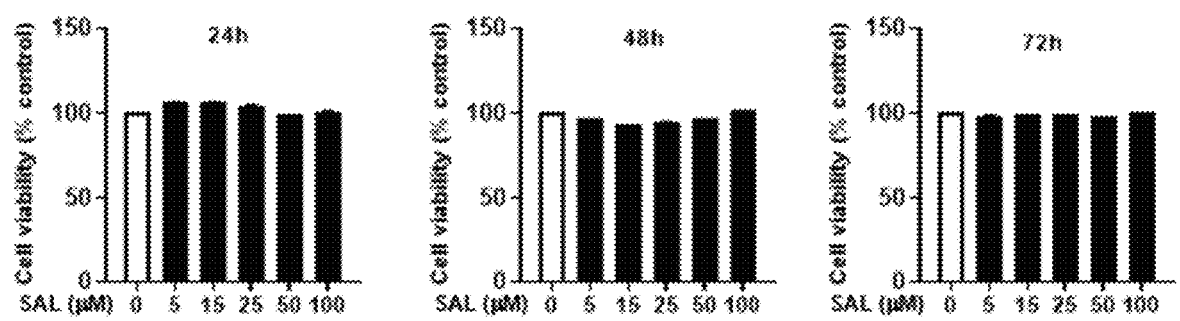

2. Experiment Results and Discussion 2.1. Result of Analysis of Change in Viability of Liver Cancer Cell Lines by Salsolinol In order to confirm the change in the viability of human-derived liver cancer cell lines (SK-HEP1 and SNU387) by the salsolinol, after culturing the human-derived liver cancer cell lines, MTT assay is performed by treatment with various concentrations of the salsolinol (refer to FIG. 1).

In the case of the SK-Hep1, which is liver cancer cell lines derived from male, after treatment with the salsolinol at various concentrations, the liver cancer cell lines are cultured for 24 hours, and as a result, it is confirmed that the cell viability decreases as the concentration of salsolinol increases. The salsolinol treatment time is increased to 48 and 72 hours, and as a result, it is confirmed that the degree of decrease in cell viability according to the treatment concentration of salsolinol increases.

On the contrary, in the case of the SNU387, which is liver cancer cell lines derived from women, it is confirmed that the cell viability is not decreased by the salsolinol, and the same result is illustrated even in the case where the treatment time with the salsolinol is increased.

Therefore, the salsolinol according to the invention is determined to inhibit the cell viability by inhibiting the cell viability of human-derived liver cancer cell lines, and in particular is determined to have an effect of specifically decreasing the activity of cells on the male-derived liver cancer cells and have no effect of inhibiting the activity of cells on the female-derived liver cancer cells.

2.2. Result of Analysis of Change in Colony Formation and Cell Migration of Liver Cancer Cell Lines by Salsolinol Based on the result that the salsolinol according to the invention inhibits the cellular activity of the SK-Hep1, which is male-derived liver cancer cell lines, the effect of the salsolinol on the colony formation ability and the cell migration ability of the male-derived liver cancer cell lines SK-Hep1 is analyzed.

Figure 2:
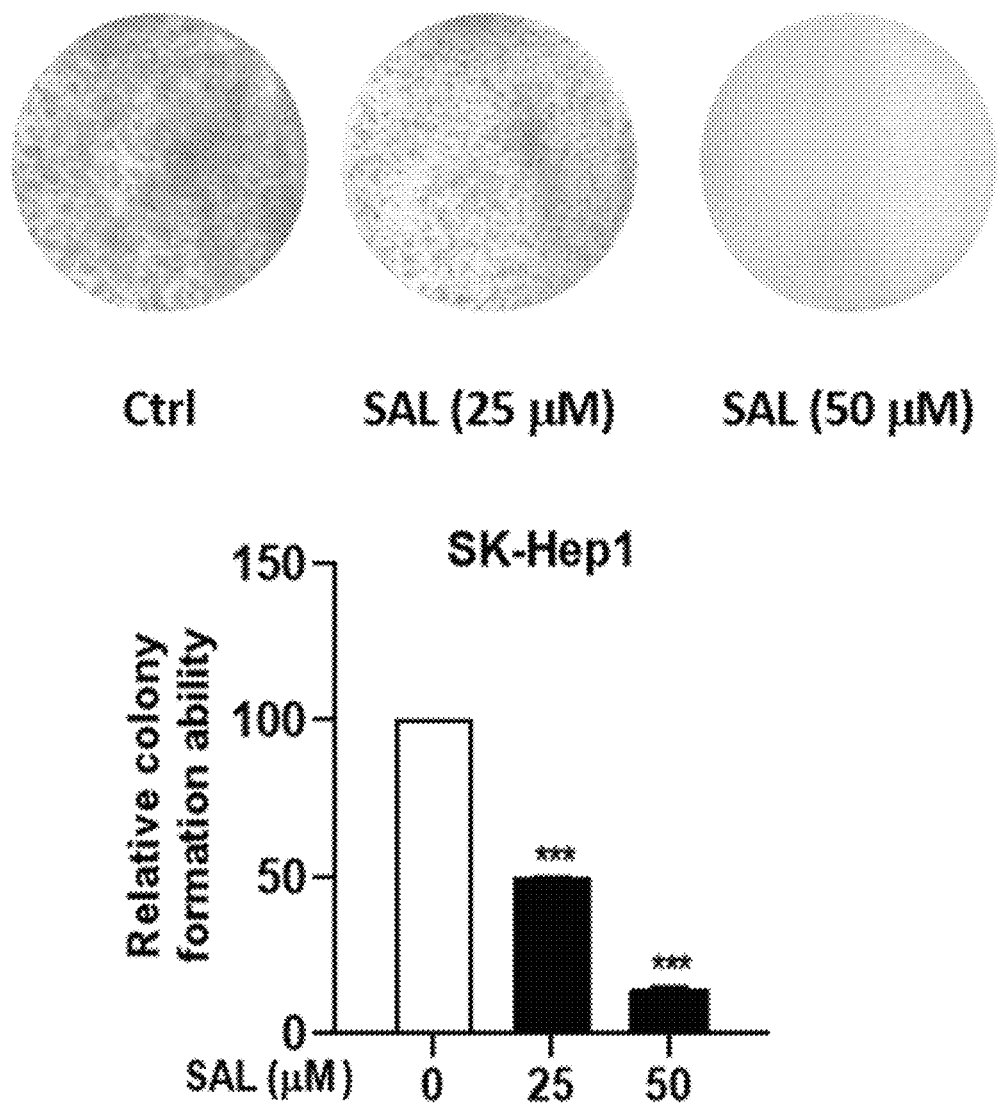
FIG. 2 illustrates results of confirming a change in colony formation ability of male-derived liver cancer cell lines (SK-Hep1) according to a concentration of salsolinol according to the invention.

After culturing the SK-Hep1 cells at $1 \times 10^4$ cells/well for 24 hours, the SK-Hep1 is treated three times at 48 hour intervals with the salsolinol so as to have a concentration of 25 μM or 50 μM, and then the degree of colony formation is checked (refer to FIG. 2).

The colony formation experiment for the SK-Hep11 is repeated a total of 4 times, the statistic process is performed, and comparison and analysis are performed. As a result of the experiment, in the case of being treated with the salsolinol having a concentration of 25 μM, it is confirmed that the colony formation ability of the SK-Hep1 is decreased to a level of 50% compared with the SK-Hep1 not treated with the salsolinol. In the case of being treated with the salsolinol having a concentration of 50 μM, it is confirmed that the colony formation ability of the SK-Hep1 is further decreased to a level of 20%.

Figure 3:
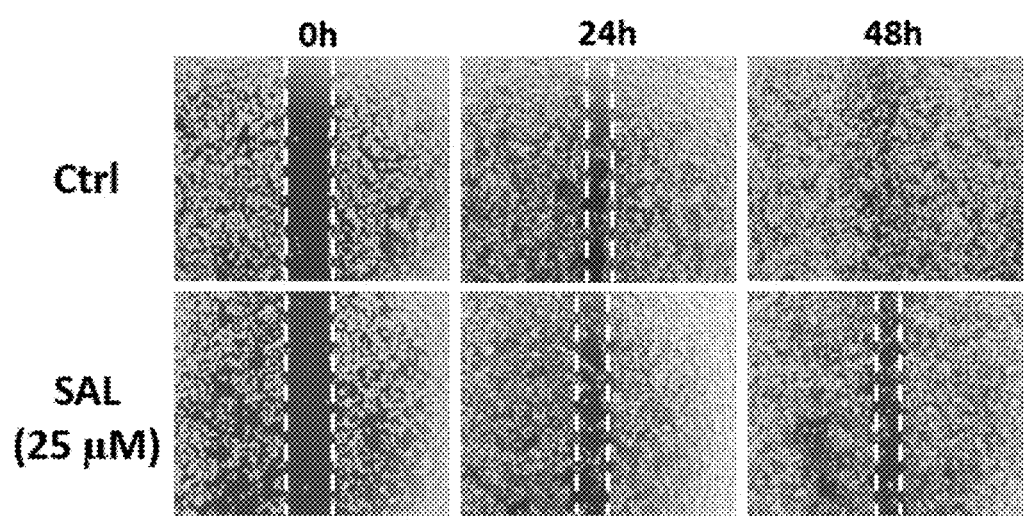
FIG. 3 illustrates results of confirming a change in cell migration of male-derived liver cancer cell lines (SK-Hep1) by the salsolinol according to the invention.

The SK-Hep1 cells are dispensed into the culture-insert so as to have a concentration of $1.5 \times 10^5$ cells, and the culturing is performed for 24 hours. After detaching the insert from the plate, each well is treated with the salsolinol so as to have a concentration of 25 μM. After the culturing is performed for 24 hours and 48 hours, and the sample is photographed by a microscope to check the cell migration ability (refer to FIG. 3). As a result of the experiment, in the case of the SK-Hep1 not treated with the salsolinol, when the culturing is performed for 24 hours, some cells are migrated, but the scratch portion is clearly distinguished. When the culturing is performed for 48 hours, a large number of SK-Hep1 cells are migrated, and it is confirmed that the scratch disappears. On the other hand, in the case of the SK-Hep1 treated with 25 μM of salsolinol, when the culturing is performed for 24 hours, it is confirmed that some cells are migrated, but the scratch portion is clearly distinguished. Even after the culturing is performed for 48 hours, it is confirmed that the scratch portion does not disappear, the boundaries of the scratches are clearly distinguished and maintained similarly to that of the culturing for 24 hours.

Accordingly, it is determined that, with respect to the male-derived liver cancer cell lines SK-Hep1, the salsolinol according to the invention decreases the ability to form colonies in a concentration-dependent manner and decreases the cell migration ability.

Figure 4:
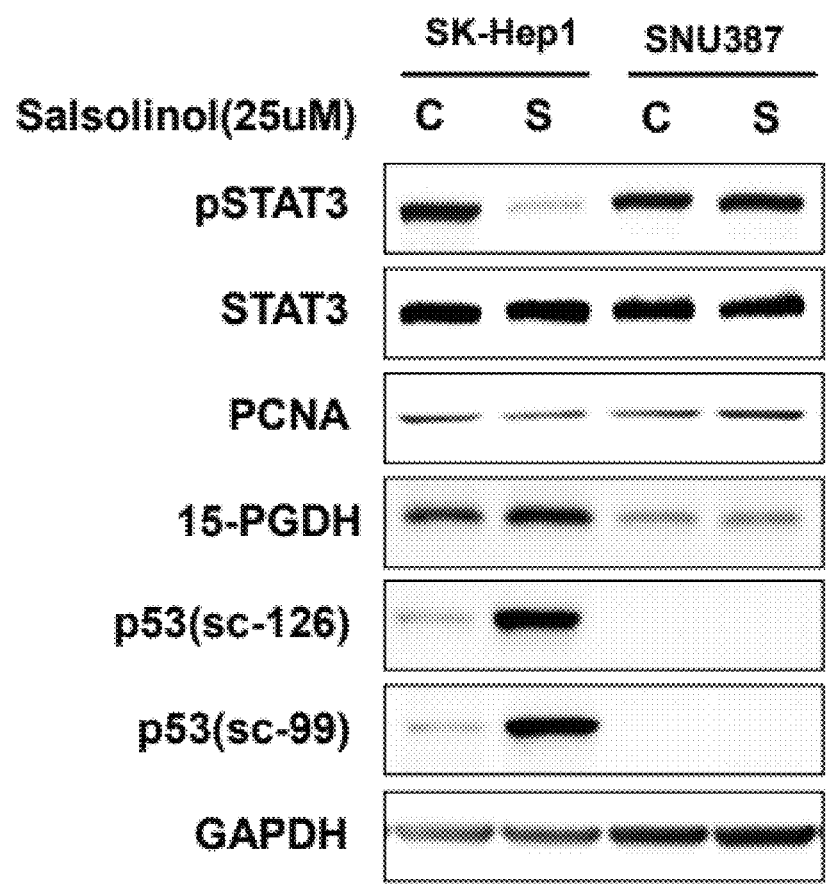
FIG. 4 illustrates results of confirming expression of tumor-related genes in male-derived liver cancer cell lines (SK-Hep1) and female-derived liver cancer cell lines (SNU387) by salsolinol according to the invention by a Western blotting method.
Figure 5:
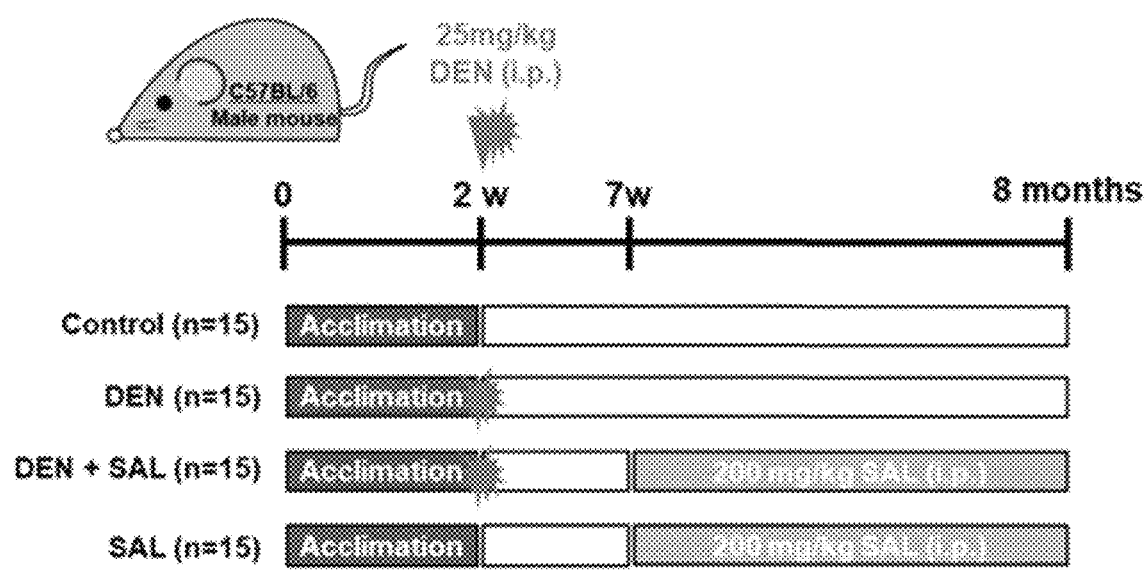
FIG. 5 illustrates a method of manufacturing a DEN-induced liver cancer animal model (male) according to the invention and administering the salsolinol to the DEN-induced liver cancer animal model.

2.3. Results of Analysis of Changes of Tumor-Related Gene Expression In Liver Cancer Cell Lines By Salsolinol As a result of the above-described experiment, it is confirmed that the activity of cells in the male-derived liver cancer cell lines SK-Hep1 is decreased by the salsolinol, and particularly, the specificity for the male-derived liver cancer cell lines is confirmed. In order to check the correlation between the decrease in the activity of cells of the liver cancer cell lines by the salsolinol and the gene expression, the SK-Hep1 which is a male-derived liver cancer cell line and the SNU387 which is a female-derived liver cancer cell line are cultured, and the samples are treated with 25 μM of salsolinol d for 72 hours. After the treatment, changes in the expression levels of tumor-related genes such as STAT3, pSTAT3, PCNA, 15-PGDH, and p53 are checked (refer to FIG. 4).

The STAT3 (Signal Transducer and Transcription 3) is continuously activated through phosphorylated STAT3 (pSTAT3) to facilitate tumor formation. In the case of the salsolinol-treated male-derived liver cancer cell lines SK-Hep1 and female-derived liver cancer cell lines SNU387, it is confirmed that the STAT3 remains constant regardless of the salsolinol-treated male-derived liver cancer cell lines SK-Hep1 and female-derived liver cancer cell lines SNU387. However, in the case of phosphorylated STAT3 (pSTAT3), it is confirmed that the expression level of the pSTAT3 in the male-derived liver cancer cell lines SK-Hep1 is decreased by treatment with the salsolinol, whereas it is confirmed that the expression level of the pSTAT3 in the female-derived liver cancer cell lines SNU387 is not decreased by the salsolinol.

The proliferating cell nuclear antigen (PCNA) is a protein that plays an important role in the proliferation process of cells, and the expression rate is increased in cancer cells. The salsolinol-treated male-derived liver cancer cell lines SK-Hep1 and female-derived liver cancer cell lines SNU387 are confirmed to have PCNA expression levels. As a result, it is confirmed that the expression level of PCNA in the SK-Hep1 is slightly decreased by the salsolinol, whereas it is confirmed that the expression level of PCNA in the SNU387 is rather increased by the salsolinol.

The 15-PGDH (15-prostaglandin dehydrogenase) is known to have an anti-inflammatory effect as a cancer inhibitor. The expression levels of 15-PGDH of the salsolinol-treated male-derived liver cancer cell lines SK-Hep1 and female-derived liver cancer cell lines SNU387 are checked. As a result, it is confirmed that the expression level of 15-PGDH in the SK-Hep1 is increased by the salsolinol, whereas it is confirmed that the expression level of 15-PGDH in the SNU387 remains constant regardless of the salsolinol.

The p53 is a representative cancer inhibitor and has an effect of inhibiting abnormal proliferation or mutation in cells. The expression levels of P53 of the salsolinol-treated male-derived liver cancer cell lines SK-Hep1 and female-derived liver cancer cell lines SNU387 are checked. As a result, it is confirmed that the expression level of p53 is increased by the salsolinol in the SK-Hep1, whereas the expression level of p53 is not changed by the salsolinol in the SNU387.

Therefore, the salsolinol according to the invention is determined to have an anticancer effect of inhibiting the activity of cancer cells by inhibiting the expression of pSTAT3 and increasing the expression of 15-PGDH and p53 for the male-derived liver cancer cell lines and is determined to have no anticancer effect on the female-derived liver cancer cell lines.

2.4. Experimental Results of DEN-Induced Liver Cancer Mouse Model

A male DEN-induced liver cancer mouse model is prepared by intraperitoneal (IP) administration of DEN 25 mg/kg, and the salsolinol 200 mg/kg is administered intraperitoneally to the model, and an effect of the salsolinol on liver cancer treatment is checked.

Figure 6A:
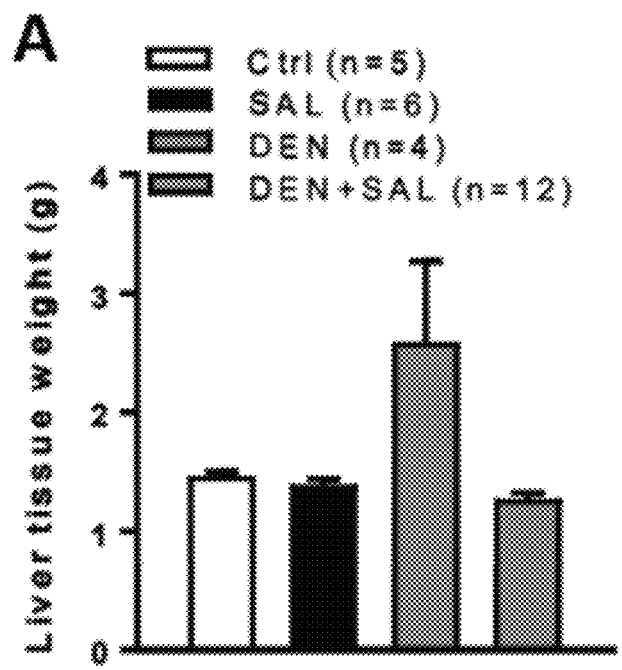
FIGS. 6A and 6B illustrate a graph of results of measuring weights of a liver of a normal mouse (male), a liver of a DEN-induced liver cancer animal model (male), a liver of a DEN-induced liver cancer animal model (male) administered with the salsolinol, and a liver of a normal mouse (male) administered intraperitoneally with only the salsolinol. Panel A illustrates a result of comparing weights of liver tissues, and Panel B illustrates a result of comparing weights of liver tissues to a weight of body.
Figure 6B:
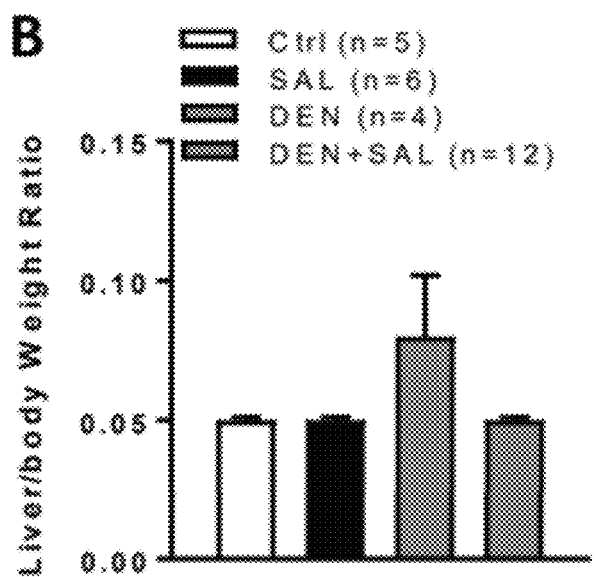

In order to check the change in the weight of liver tissue due to the occurrence and treatment of liver cancer, the normal mouse (male, ctrl, n=5), the DEN-induced liver cancer animal model (male, DEN, n=4), the DEN-induced liver cancer animal model (male, DEN+SAL, n=12) administered with the salsolinol, and the normal mouse (SAL, n=6) administered intraperitoneally with the salsolinol alone are sacrificed, the livers are excised, and the weights are measured and compared (refer to FIG. 6). As a result of the experiment, it is confirmed that the weight of the liver tissue of the DEN-induced liver cancer mouse model is increased by about 60% compared with the weight of the liver tissue of the normal mouse. On the contrary, in the case of the DEN-induced liver cancer animal model administered intraperitoneally with the salsolinol, it is confirmed that the weight of the liver tissue is slightly equal to that of the normal mouse and the normal mouse administered with the salsolinol alone.

The above-described results denote that the cancer in the liver tissue is removed by administering the salsolinol to the DEN-induced liver cancer mouse model.

Figure 7:
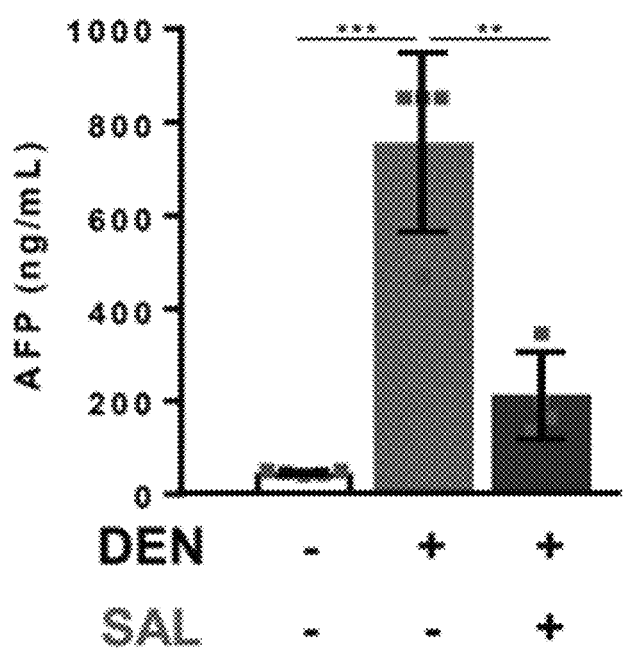
FIG. 7 illustrates results of measuring the amount of α-fetoprotein (AFP) expressed in the DEN-induced liver cancer animal model (male) according to the invention.

Alpha-fetoprotein (AFP) is a type of serum protein that is normally produced in a fetus. In the case of an adult, the AFP is increased in liver cancer or tumors of germ cells derived from egg yolk, so that the measured value of the AFP can be used for decision of disease stage and determination of treatment effect. Blood is collected from the normal mouse (n=5), the DEN-induced liver cancer mouse model (n=4), and the DEN-induced liver cancer mouse model (n=4) administered with the salsolinol, and the AFP levels are analyzed. As a result, it is confirmed that the AFP level of the normal mouse is at a level of 50 ng/ml, whereas the AFP level of the DEN-induced liver cancer mouse model reached an average level of 720 ng/ml, the AFP level of the DEN-induced liver cancer mouse model administered with the salsolinol is decreased to an average AFP level of 200 ng/ml (refer to FIG. 7). The results denote that the liver cancer is cured as the liver cancer tissue disappears as the DEN-induced liver cancer mouse model is administered with the salsolinol.

The normal mouse (ctrl), the DEN-induced liver cancer mouse model (DEN), the DEN-induced liver cancer mouse model administered with the salsolinol (DEN+SAL), and the normal mouse administered with the salsolinol (SAL) are sacrificed, and the livers are excised. The liver cancer tissues formed on the surfaces of the liver tissues are observed, and H&E tissue staining is performed to check the liver tissues (refer to FIG. 8). As a result of the experiment, no liver cancer tissue is found on the liver surface of the normal mouse and on the liver surface of the normal mouse to which the salsolinol is administered, and an average of about 10 liver cancer tissues are observed on the liver surface of the DEN-induced liver cancer mouse model. In particular, in a case where the DEN-induced liver cancer mouse model is administered with the salsolinol, an average of four liver cancer tissues are observed on the liver surface, and thus, the number of liver cancer tissues is confirmed to be decreased by about 60% compared with that of the DEN-induced liver cancer mouse model (refer to FIG. 8). In addition, H&E staining is performed on the liver tissues of the mice. As a result, abnormal types of hepatocytes observed in the liver tissue of the DEN-induced liver cancer mouse model are not observed in the liver tissue administered with the salsolinol.

Therefore, the salsolinol according to the invention is administered to a mouse model in which the outbreak of liver cancer is induced by intraperitoneally administering the DEN to decrease liver cancer tissues and decrease the AFP levels, so that the salsolinol is determined to be usable as a treatment for liver cancer.

2.5. Analysis of Changes In Tumor-Related Gene Expression In DEN-Induced Liver Cancer Mouse Model By Salsolinol In order to check the liver cancer therapeutic effect of the salsolinol confirmed through the above-described animal experiments at the genetic level, tumor-related genes expressed in liver tissues of the normal mouse (male, ctrl), the DEN-induced liver cancer animal model (male, DEN), and the DEN-induced liver cancer animal model (male, DEN+SAL) administered with the salsolinol are checked, and comparison and analysis are performed.

Figure 9:
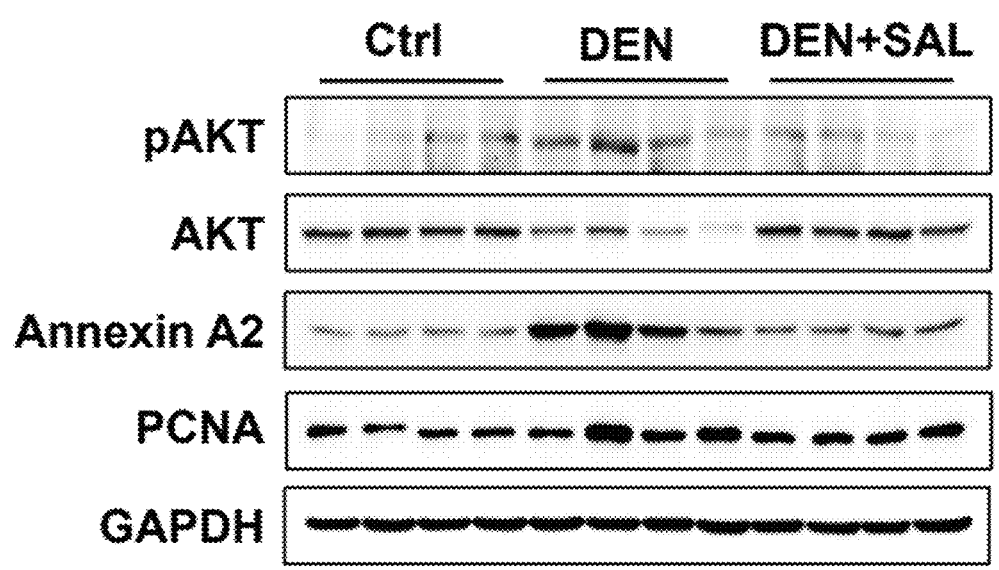
FIG. 9 illustrates results of analysis the amount of genes expressed in the liver tissue of the normal mouse (male), the liver tissue of the DEN-induced liver cancer animal model (male), and the liver tissue of the DEN-induced liver cancer animal model (male) administered with the salsolinol according to the invention by using a Western blotting method.

The normal mouse, the DEN-induced liver cancer mouse model, and the DEN-induced liver cancer mouse model administered with the salsolinol are sacrificed, the livers are excised, the liver tissues are crushed, and the proteins are extracted. After separating the extracted protein through electrophoresis, the expression levels of tumor-related genes AKT, p-AKT, Annexin A2, and PCNA and the changes in the expression levels are analyzed by using a Western blotting method (refer to FIG. 9).

It is confirmed that the expression level of p-AKT, that is, the degree of phosphorylation of AKT in the DEN-induced liver cancer mouse model is increased compared with that of the normal mouse, whereas it is confirmed that the degree of phosphorylation of AKT in the DEN-induced liver cancer mouse model administered with the salsolinol is decreased to the level of the normal mouse.

Annexin A2 is known to be overexpressed in various carcinomas and has been studied as a biomarker for cancer diagnosis. In the invention, the expression level of Annexin A2 is measured, and the effect of the salsolinol on liver cancer treatment is confirmed. As a result of the experiment, it is confirmed that the expression level of Annexin A2 in the DEN-induced liver cancer mouse model is increased rapidly compared with the normal mouse, whereas it is confirmed that the expression level of Annexin A2 in the DEN-induced liver cancer mouse model administered with the salsolinol is decreased.

The expression level of PCNA is checked, and as a result, it is confirmed that the expression level of PCNA in the DEN-induced liver cancer mouse model is increased compared with that of the normal mouse, whereas it is confirmed that the expression level of PCNA in the DEN-induced liver cancer mouse model administered with the salsolinol is decreased to the level of the normal mouse.

Figure 10:
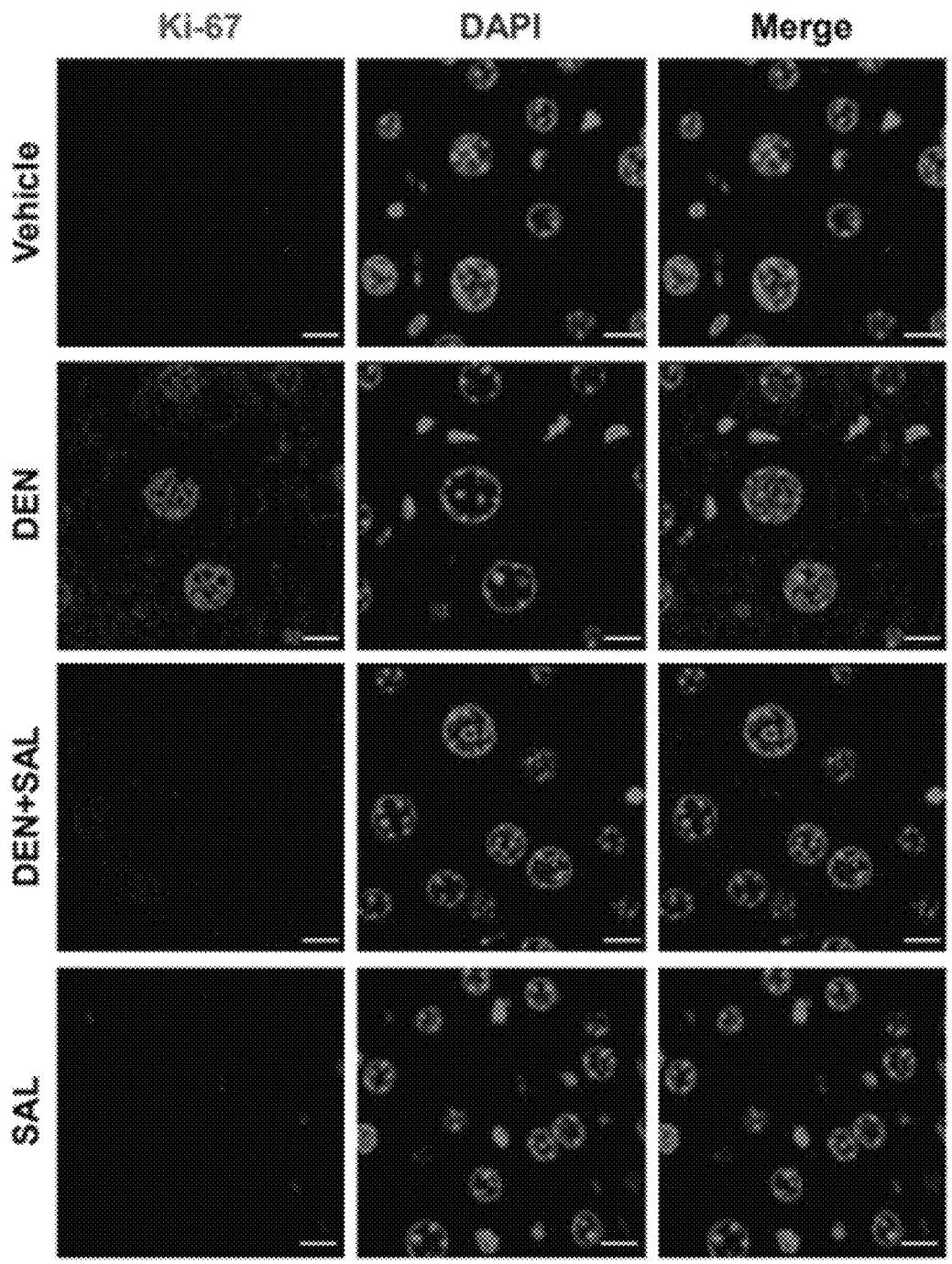
FIG. 10 illustrates results of analyzing a cancer cell proliferation marker Ki-67 expressed in a liver tissue of a DEN-induced liver cancer animal model (male), a liver tissue of a DEN-induced liver cancer animal model (male) administered with salsolinol, and a liver tissue of a normal mouse (male) administered with the salsolinol according to the invention by using an immunofluorescence staining method.
Figure 11:
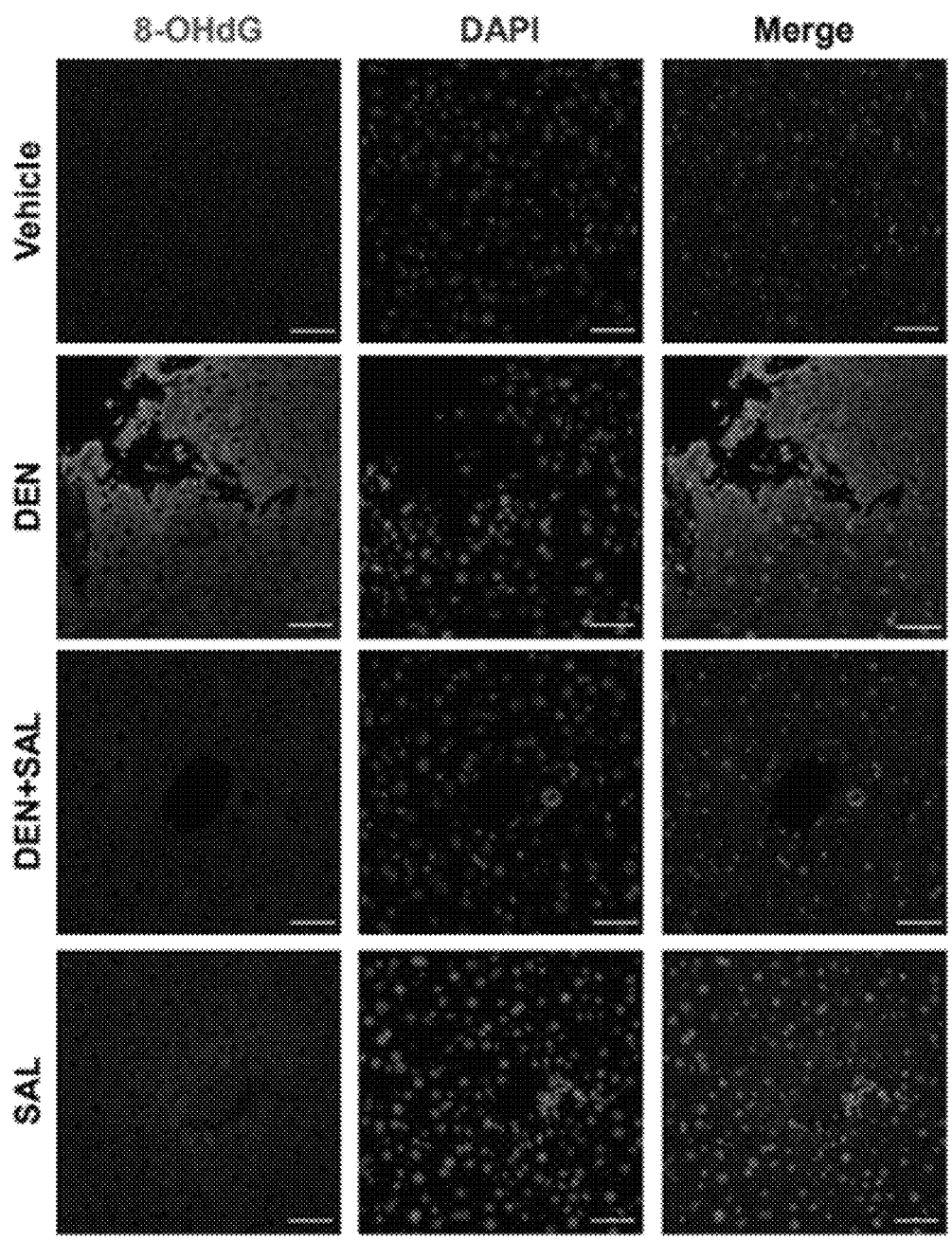
FIG. 11 illustrates results of analyzing oxidative stress and cancer marker 8-OHdG expressed in a liver tissue of a DEN-induced liver cancer animal model (male), a liver tissue of a DEN-induced liver cancer animal model (male) administered with salsolinol, and a liver tissue of a normal mouse (male) administered with the salsolinol according to the invention by using an immunofluorescence staining method.

Tumor-related genes Ki-67 and 8-OHdG expressed in the liver tissue of the DEN-induced liver cancer mouse model (male, DEN), the DEN-induced liver cancer mouse model (male, DEN+SAL) administered with the salsolinol, and the normal mouse (male, SAL) administered with the salsolinol are analyzed by using an immunofluorescence measurement method (refer to FIGS. 10 and 11).

The Ki-67 is not expressed in a quiescent period (G0 period) of the cell cycle, but it is expressed only in a proliferative period (G1, S, G2, and M period), so that the Ki-67 is closely related to the proliferation of tumor cells. Therefore, Ki-67 is used as a cancer diagnostic marker to evaluate the cancer prognosis and to evaluate the grade of cancer cells. As a result of the experiment, overexpression of Ki-67 is confirmed in the cell nucleus in the liver tissue of the DEN-induced liver cancer mouse model, whereas the expression of Ki-67 is not confirmed in the liver surface of the DEN-induced liver cancer mouse model administered with the salsolinol and in the liver tissue of the normal mouse administered with the salsolinol (refer to FIG. 10).

The 8-OHdG (8-hydroxydeoxyguanosine) is a by-product generated in a DNA repair process that corrects DNA mutations in cells, and a high concentration of the 8-OHdG is observed when DNA damage is large. Therefore, by checking the expression level of 8-OHdG, cancer diagnosis is possible. As a result of the experiment, overexpression of 8-OHdG in the cytoplasm is confirmed in the liver tissue of the DEN-induced liver cancer mouse model, whereas the expression of 8-OHdG is conformed to be at a low level in the liver tissue of the DEN-induced liver cancer mouse model administered with the salsolinol and in the liver tissue of the normal mouse administered with the salsolinol (refer to FIG. 11).

Figure 12:
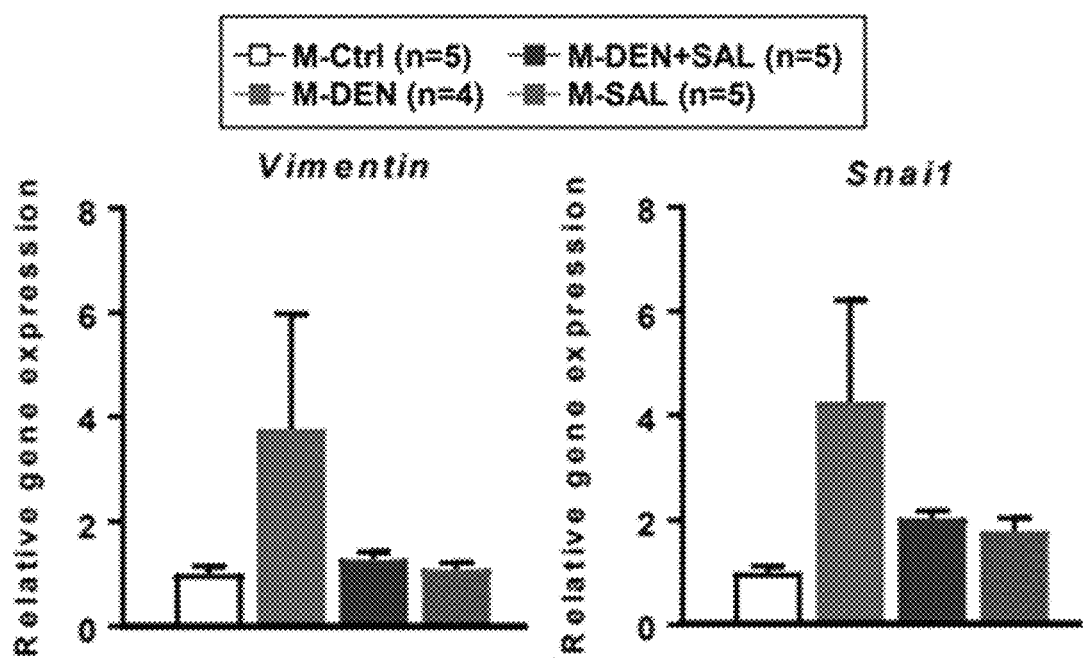
FIG. 12 illustrates results of analyzing the amount of genes (Snai1 and Vimentin) expressed in a liver of a normal mouse (male), a liver of a DEN-induced liver cancer animal model (male), a liver of a DEN-induced liver cancer animal model (male) administered with salsolinol, and a liver of a normal mouse (male) administered with the salsolinol according to the invention.
Figure 13:
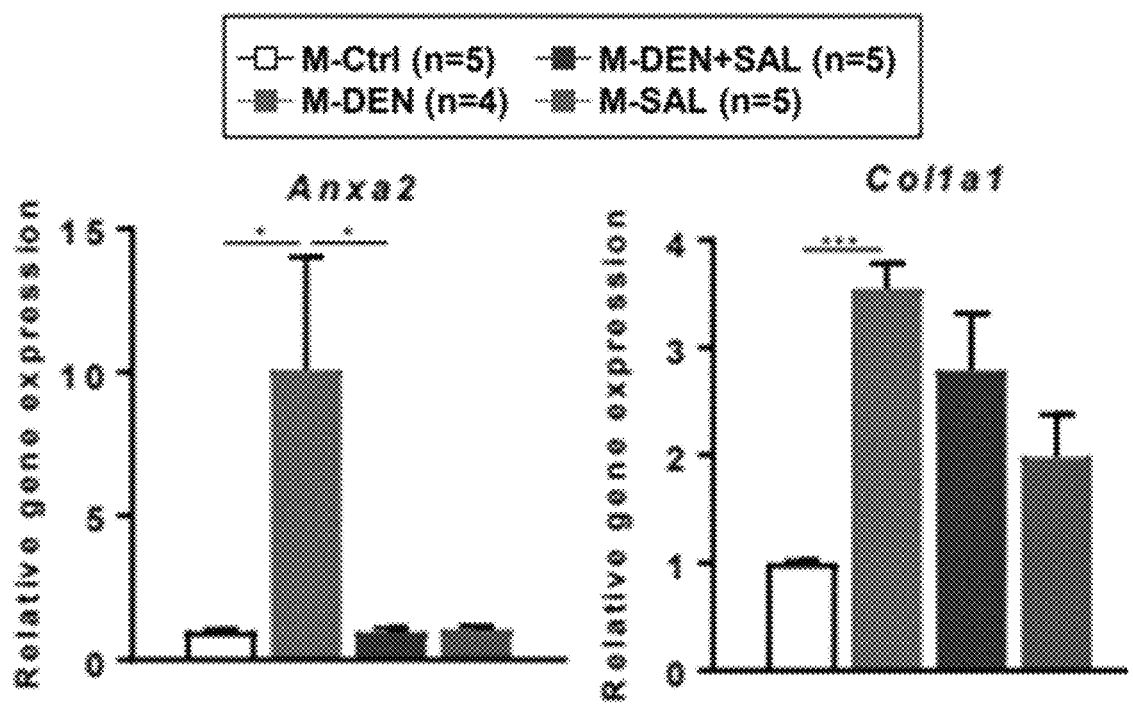
FIG. 13 illustrates results of analyzing the amount of genes (Anxa2 and Col1a1) expressed in a liver of a normal mouse (male), a liver of a DEN-induced liver cancer animal model (male), a liver of a DEN-induced liver cancer animal model (male) administered with salsolinol, and a liver of a normal mouse (male) administered with the salsolinol according to the invention.

The normal mouse (male, M-Ctrl, n=5), the DEN-induced liver cancer mouse model (male, M-DEN, n=4), the DEN-induced liver cancer mouse model administered with the salsolinol (male, M-DEN-SAL), n=5), and the normal mouse administered with the salsolinol (male, M-SAL, n=5) are sacrificed, and the livers are excised. After crushing the liver tissues, the expression levels of the Snai1 gene (coding for SNAI1), the Vimentin gene (or VIM, Coding for Vimentin), the Anxa2 gene (coding for Annexin A2), and the Col1a1 gene (coding for Collagen type I alpha 1) are quantitatively analyzed by using a real-time quantitative polymerase chain reaction method (refer to FIGS. 12 and 13).

As a result of the experiment, in the case of the Snai1 and Vimentin genes, it is confirmed that the expression level is increased in the DEN-induced liver cancer mouse model, whereas it is confirmed that the expression level in the DEN-induced liver cancer mouse model administered with the salsolinol is decreased to the expression level of expression in the normal mouse that is not treated with the salsolinol. The Snai1 is formed by encoding the genetic information of SNAI1 and is known to induce cancer recurrence in the case of the overexpression, and the Vimentin is formed by encoding the genetic information of Vimentin and is known to be overexpressed during cancer metastasis.

Therefore, when the DEN-induced liver cancer mouse model is treated with the salsolinol according to the invention, it is confirmed that the expression levels of tumor-related genes pAKT, Annexin A2, PCNA, Ki-67, 8-OHdG, SNAI2, Vimentin, and Annexin A2 are decreased to the expression level of the normal mouse to inhibit the proliferation of hepatocellular carcinoma cell lines.

3. Conclusions

In the invention, the effect of the salsolinol on the treatment of liver cancer is experimentally demonstrated by using liver cancer cell lines and a liver cancer mouse model using DEN.

First, according to the results of cell experiments using liver cancer cell lines, it is confirmed that the salsolinol according to the invention is specific to the male-derived liver cancer cell lines SK-Hep1 and decreases the proliferation ability and colony formation ability of cancer cells in a concentration-dependent manner and it is confirmed that the salsolinol according to the invention also inhibits metastatic ability of the cancer cells. In addition, it is confirmed that, when the male-derived liver cancer cell lines SK-Hep1 is treated with the salsolinol according to the invention, the expression level of p-STAT3, which is a tumor-related gene, decreases, and the expression levels of p53 and 15-PGDH, which are tumor inhibitor genes, increase.

Next, according to the results of animal experiments using the DEN-induced liver cancer mouse model, when the DEN-induced liver cancer mouse model is administered with the salsolinol, it is confirmed that the number of tumors that are outbroken in the liver is rapidly decreased, and it is confirmed that the level of AFP for diagnosing the liver cancer is also decreased. In addition, when the salsolinol according to the invention is administered, it is confirmed that the expression levels of tumor-related genes pAKT, Annexin A2, PCNA, Ki-67, 8-OHdG, SNAI2, Vimentin, and Annexin A2, of which expression levels have been increased due to the outbreak of liver cancer are decreased to the expression level of the normal mouse from which the liver cancer is not outbroken. Therefore, since the salsolinol according to the invention has the effect of reducing the expression of tumor-related genes indicating the outbreak and progression of the liver cancer and increasing the expression levels of anticancer and anti-inflammatory genes that inhibit tumor cell proliferation, it is determined that it is possible to provide a composition for treating liver cancer together with acceptable pharmaceutical salts.

The specific embodiments described in this specification are meant to represent preferred embodiments or examples of the invention, and the scope of the invention is not limited thereto. It will be apparent to those skilled in the art that variations and other uses of the invention do not depart from the scope of the invention described in the claims of the specification.

What is claimed is:

1. A method for treating a liver cancer, comprising:
   administering to a subject in need thereof a therapeutically effective amount of a composition comprising salsolinol,
   wherein the liver cancer is male-derived liver cancer.

2. The method according to claim 1, wherein the subject is male.

3. The method according to claim 1, wherein the composition inhibits phosphorylation of STAT3, phosphorylation of AKT, expression of Annexin 2, expression of PCNA, expression of Ki-67, expression of 8-OHdG, expression of SNAI2, and expression of Vimentin and increases expression of 15-PGDH and expression of p53 to inhibit proliferation of male-derived liver cancer cells.

4. The method according to claim 1, wherein the composition increases expression of 15-PGDH to alleviate an inflammatory response of male-derived liver cancer cells.

5. A method for improving an alcoholic liver disease, comprising:
   administering to a subject in need thereof a therapeutically effective amount of a food composition comprising salsolinol.

6. The method according to claim 5, wherein the food composition has an effect of specifically improving a male-derived alcoholic liver disease.

7. The method according to claim 5, wherein the subject is male.

* * * * *